(12) United States Patent
Lee et al.

(10) Patent No.: US 6,230,080 B1
(45) Date of Patent: May 8, 2001

(54) MONITORING SYSTEM AND MONITORING METHOD FOR A CLEAN ROOM REGULATING SYSTEM

(75) Inventors: Jung-sun Lee, Suwon; Ki-hwan Lim, Yongin; Yo-han An, Sungnam; Jae-heung Choi, Yongin, all of (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/066,107

(22) Filed: Apr. 24, 1998

(30) Foreign Application Priority Data

May 2, 1997 (KR) .................................................. 97-17064

(51) Int. Cl.[7] ........................... G06F 13/00; G06F 15/00; G06F 21/00
(52) U.S. Cl. ......................... 700/275; 700/121; 700/274; 55/356; 55/385.2; 454/187
(58) Field of Search .................................. 700/275, 276, 700/121; 55/356, 385.2; 454/187

(56) References Cited

U.S. PATENT DOCUMENTS

| | | | |
|---|---|---|---|
| 4,688,183 | * 8/1987 | Carll et al. | 364/554 |
| 5,444,637 | * 8/1995 | Smesny et al. | 702/127 |
| 5,518,451 | * 5/1996 | Renz et al. | 454/187 |
| 5,553,006 | * 9/1996 | Benda | 364/550 |
| 5,572,533 | * 11/1996 | Sunada et al. | 371/20.1 |
| 5,764,146 | * 6/1998 | Baldwin et al. | 340/567 |
| 5,798,945 | * 8/1998 | Benda | 364/550 |
| 5,858,041 | * 1/1999 | Luetkemeyer | 55/385.2 |
| 5,862,054 | * 1/1999 | Li | 700/121 |
| 5,943,231 | * 8/1999 | Thomas | 364/148 |
| 5,966,674 | * 10/1999 | Crawford et al. | 702/47 |
| 5,971,597 | * 10/1999 | Baldwin et al. | 364/528.12 |
| 6,099,607 | * 8/2000 | Haslebacher | 55/356 |

OTHER PUBLICATIONS

IBM Technical Disclosure Bulletin vol. 36 No. 11, Nov. 1993.*

* cited by examiner

*Primary Examiner*—Ayaz Sheikh
*Assistant Examiner*—Frantz B. Jean
(74) *Attorney, Agent, or Firm*—Jones Volentine, L.L.C.

(57) ABSTRACT

A monitoring system and method for monitoring a clean room regulating system. The monitoring system includes a particle counter with a pump having a pumping state for pumping a fluid containing particles. The particle counter produces an analog particle signal indicative of an amount of particles detected. The particle counter also produces a pump-state signal corresponding to the pumping state. A signal processor is included for converting the analog particle signal into a first digital signal, for converting the pump-state signal into an analog pumping signal, and for converting the analog pumping signal into a second digital signal. A host computer is included for receiving the first digital signal and deriving the amount of particles detected, for receiving the second digital signal and deriving the pumping state, and for monitoring the pumping state and the amount of particles counted. The system includes a communication channel for transferring the first digital signal and the second digital signal from the signal processor to the host computer.

20 Claims, 3 Drawing Sheets

MONITORING SYSTEM AND MONITORING METHOD FOR A CLEAN ROOM REGULATING SYSTEM

BACKGROUND OF THE INVENTION

1. Field of the Invention

The present invention relates to a monitoring system and method for monitoring a clean room regulating system. More particularly, the monitoring system determines the operational state of the regulating system by transferring signals from the regulating system through an interface to a host computer.

2. Description of the Related Art

High-tech industries including the electronics industry require a clean, consistently maintained fabrication environment which meets certain cleanliness criteria. Most of the fabrication processes of highly-integrated semiconductor devices are carried out in such "clean rooms." Clean room conditions, including temperature, humidity, air flow rate, pressure difference and particle distributions, can greatly affect the yield of semiconductor device production. Therefore, air quality in a clean room should be regularly checked to ensure that cleanliness criteria in terms of number of particles per unit volume are being met. Other air quality parameters such as air temperature, humidity, flow rate, and pressure also should be checked by a regulating system. Such a system therefore includes sensors for detecting the temperature and humidity of air in the clean room, a sensor for detecting the flow rate of air, a sensor for sensing the pressure difference between the inside and outside of the clean room, and a set of particle counters for checking the particle content in several sample volumes of air from which the distribution of particles inside the clean room can be inferred. Accordingly, these conditions are monitored using the above sensors.

However, such precise monitoring cannot be performed when any of the sensors of the regulating system, especially a particle counter, is not operating normally. Therefore, the sensors, especially the particle counters, should be periodically checked. This is usually done by a check performed at the site of the sensor. Because periodic checking at the site is difficult, it is often not performed until after the sensor has been operating in an abnormal state for some time. As a result, much of the data monitored from the regulating system is unreliable for the time period between the last periodic check and the discovery of an abnormally operating sensor.

Accordingly, there is a need for a more efficient means of monitoring both a clean room maintained by a regulating system and the sensors of the regulating system itself.

SUMMARY OF THE INVENTION

The present invention is directed to a monitoring system and method for checking a clean room and regulating system which substantially overcomes one or more of the problems presented by prior art systems and methods. Another object of the present invention is to provide a monitoring system for checking the abnormal state of a clean room regulating system by providing the clean room's host computer with a self-examination function.

To achieve these and other advantages and in accordance with the purposes of the present invention, a monitoring system for monitoring a clean room regulating system, comprises a particle counter comprising a pump having a pumping state for pumping a fluid containing particles. The particle counter counts particles in the fluid and produces an analog particle signal indicative of an amount of particles detected. The particle counter also produces a pump-state signal corresponding to the pumping state. A signal processor is included for converting the analog particle signal into a first digital signal, for converting the pump-state signal into an analog pumping signal, and for converting the analog pumping signal into a second digital signal. A host computer is included for receiving the first digital signal and deriving the amount of particles detected, for receiving the second digital signal and deriving the pumping state, and for monitoring the pumping state and the amount of particles counted. A communication channel is also included for transferring the digital signals from the signal processor to the host computer.

Another aspect of the invention is a method for monitoring a clean room regulating system. The method includes choosing a self-examination function for checking a particle counter of a clean room regulating system, and selecting a particle counter to be monitored. Then the method involves monitoring a first digital signal corresponding to an amount of particles detected by the selected particle counter, and a second digital signal corresponding to a pumping state of the selected particle counter. The next step involves executing the self-examination function using the amount of particles detected, derived from the first digital signal, and using the pumping state, derived from the second digital signal. The results of the executed self-examination function are then displayed.

BRIEF DESCRIPTION OF THE DRAWINGS

The invention is described in detail with reference to the accompanying drawings, in which.

DETAILED DESCRIPTION OF THE PREFERRED EMBODIMENTS

The present invention provides a means for both monitoring the regulating system and periodically checking whether the sensors in the regulating system are operating normally. One set of embodiments of the present invention, the LAN embodiments (FIG. 1), utilizes a local area network (LAN) as a communication channel to communicate signals between the regulating system sensors and a host computer. A second set of embodiments, the direct interface embodiments (FIG. 3), utilizes a direct interface as the communication channel between the regulating system sensors and the host computer.

Figure 1:
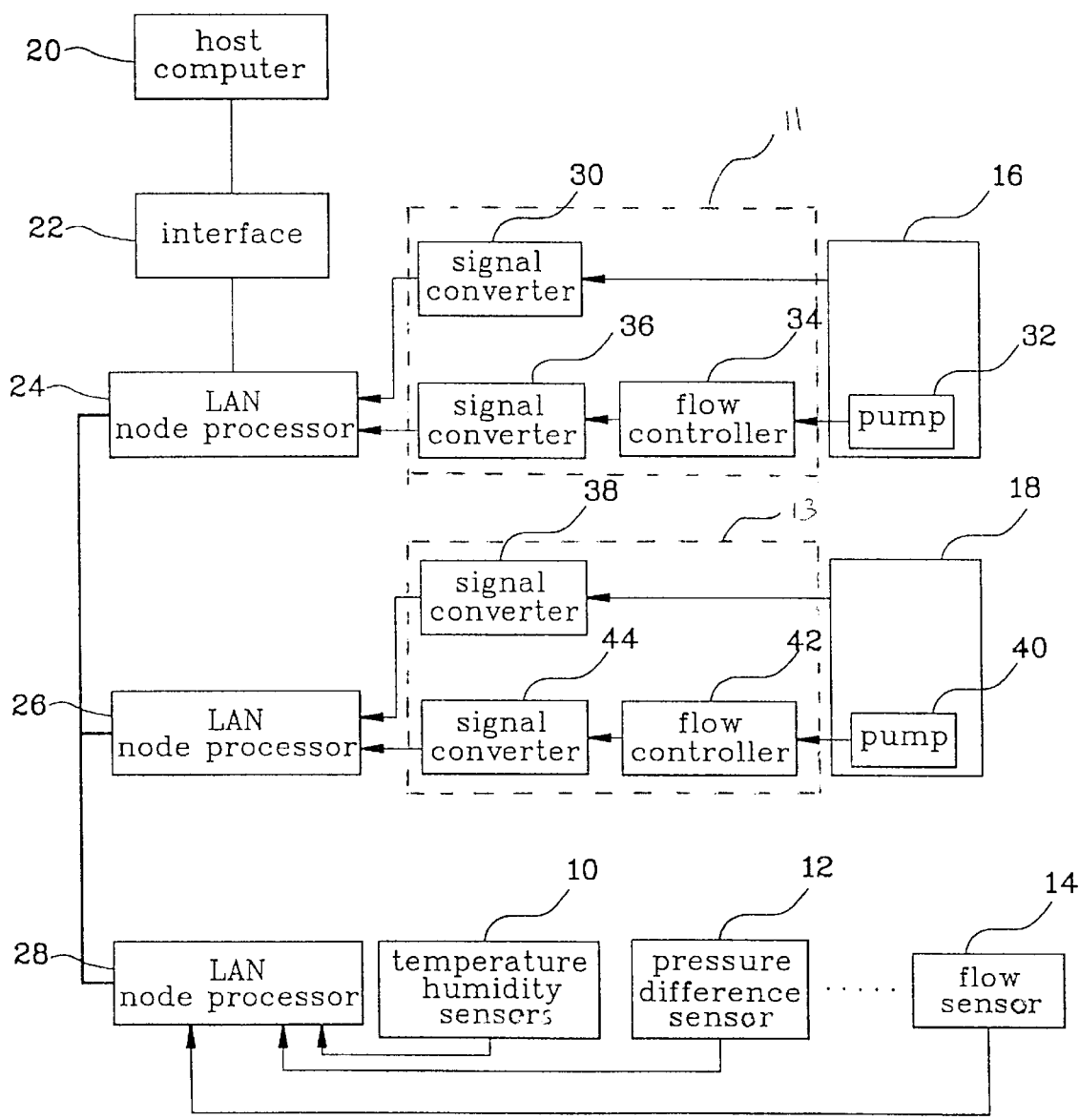
FIG. 1 is a block diagram of one embodiment of the monitoring system according to the present invention for monitoring a clean room regulating system using a local area network (LAN)

FIG. 1 depicts the structure and the operation of one of the LAN embodiments; and also illustrates many general features of the present invention. In either the LAN or direct interface embodiments, various sensors are installed inside the clean room, including a temperature sensor and humidity sensor 10, a pressure difference sensor 12, a flow rate sensor 14, and one or more particle counters 16 and 18. A host computer 20 is used for comparing the physical properties measured by the various sensors and counters and for generating an alarm signal when the clean room conditions sensed are outside specified criteria.

In the LAN embodiments, the host computer 20 is connected to one LAN Node Processor 24 through an interface 22 and that LAN Node Processor 24 is connected to others in a communications network—for example, two other LAN Node Processors 26 and 28 are depicted in FIG. 1. The communications network can use an X series interface protocol like RS-485, or a V series interface protocol, like RS-232-C.

In both LAN and direct interface embodiments, a particle counter 16 produces a particle signal, for example, an analog signal in the range from about 0 volts (V) to about 10 V that is proportional to the particle count. The analog particle signal is then fed into a signal processor 11. In the preferred embodiment, the signal processor 11 includes a first signal converter 30. The first signal converter 30 converts the input analog signal into a digital signal using the RS-232-C protocol with a voltage range from about 0 V to about 5 V and a current range from about 4 milliamperes (mA) to about 20 mA. The digital signal is input into the communication channel. In the LAN embodiments the communication channel includes the LAN Node Processor 24.

For both the LAN and direct interface embodiments, the particle counter 16 includes a pump 32 to pump a fluid such as air or other gas containing particles. Most diagnostic checks of the particle counter, i.e., most self-examination functions, involve combining the measurement of the amount of particles detected with information about the state of the pump, i.e., the pumping state. Therefore the present invention includes a particle counter that generates a pump-state signal corresponding to the pumping state. In the preferred embodiments, for both the LAN and direct interface embodiments, the pumping state utilized is the amount of fluid being pumped per unit time.

In the present invention, the signal processor 11 also converts the pump-state signal, first into an analog pumping signal and then into a second digital signal which is passed into the communication channel. In the preferred embodiments of both the LAN and direct interface embodiments, the signal processor 11 includes a flow controller 34 which detects the amount of the fluid pumped by the pump 32 and converts the amount into an analog pumping signal. In these preferred embodiments, the analog pumping signal is supplied to a second signal converter 36 in the signal processor 11. The second signal converter 36 converts the analog pumping signal into a second digital signal that also uses the RS-232-C communication protocol which is used by the first signal converter 30. The second digital signal is transferred to the communication channel. In the LAN embodiments, the communication channel includes the LAN Node Processor 24.

In the LAN embodiments, other LAN Node Processors are connected to other sensors. For example, between LAN Node Processor 26 and another particle counter 18 another signal processor 13 is disposed. In the preferred embodiment, the signal processor 13 includes another first signal converter 38, another flow controller 42, and another second signal converter 44 which operate as described with reference to the signal processor 11 above. In addition, temperature and humidity sensors 10, a pressure difference sensor 12, and a flow rate sensor 14 are connected to another LAN Node Processor, for example LAN Node Processor 28, again using the RS-232-C communication protocol.

In other LAN embodiments according to the present invention, the connection of particle counters 16, 18, LAN Node Processors 24, 26, 28 and sensors 10, 12, 14 can be duplicated or varied if necessary. The signal transmission among the LAN Node Processors 24, 26, 28 is digital. In the LAN embodiments, the signals are transferred among the plurality of LAN Node Processors using an X series interface protocol, preferably the RS-485 protocol, and thus the LAN Node Processors 24, 26, 28 convert the digital signals into network signals using the RS-485 protocol for transmission on the network. One of the LAN Node Processors is connected to the host computer 20 through an interface 22 using any appropriate protocol.

In either the LAN embodiments or the direct interface embodiments, the particle counter 16 is preferably an optical particle counter. When one or more of the particle counters 16 or 18 counts particles optically, the intensity of the light source used, such as a Helium-Neon (He—Ne) light source, semiconductor diode light source, or an Argon (Ar) laser light source, is output from the counter as an analog light-source signal corresponding to and indicative of the intensity of the light source. This signal is used to monitor the performance of the particle counter in a self-examination or diagnostic function. Therefore the present invention converts this analog light-source signal, when present, into a third digital signal via one of the signal converters, and the third digital signal is sent to the host computer 20 through the communication channel where the host computer 20 monitors it.

As described above the present invention monitors the inside environment of the clean room and the operational state of a particle counter 16 or 18 through the host computer 20. The host computer 20 derives, compares and computes logic-sums of various signals input from the temperature and humidity sensors 10, the pressure difference sensor 12, the flow rate sensor 14, and the particle counters 16 and 18. Thereby the host computer 20 can both monitor the gaseous environment of the clean room, and perform the diagnostic, self-examination functions on the sensors and particle counters.

One self-examination function compares the counted results generated by the particle counters 16 and 18 with the pumping state, all derived from the digital signals transmitted to the host computer 20 through the communication channel. The host computer 20 thus monitors whether the normal pumping and counting operations are occurring. When optical particle counters are utilized, the self-examination function performed by the host computer 20 also includes monitoring the light intensity of the source derived from the third digital signal from each optical particle counter.

Figure 2:
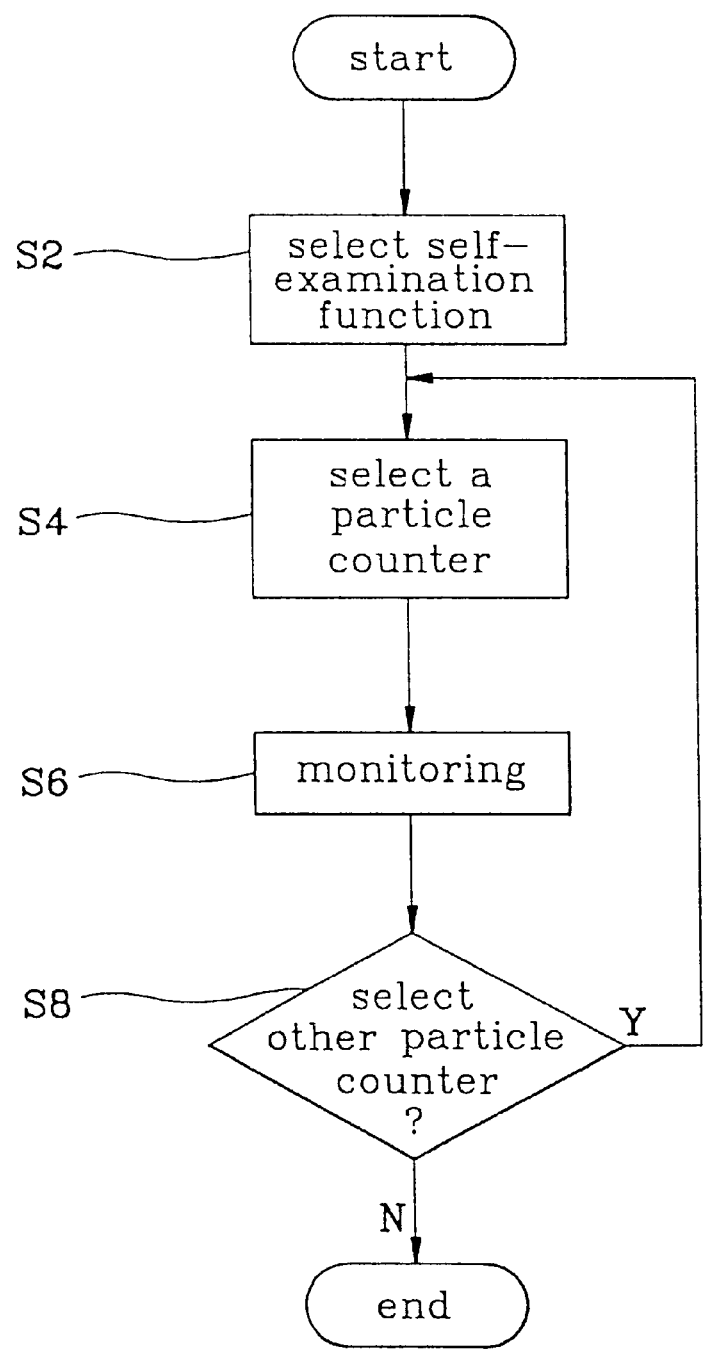
FIG. 2 is a flow chart showing the method according to the present invention for monitoring a clean room regulating system using the monitoring system of the present invention.

In the present invention, the host computer 20 is used for managing at least one clean room. Using the host computer 20 according to the present invention, a single operator can easily monitor both the clean room environment and the operating state of the regulating system, including the particle counters. When the operator performs a self-examination function for a particle counter using the host-computer 20, the steps shown in FIG. 2 are followed.

First, the self-examination function is selected in step S2 and then the particle counter to be checked is selected in step S4. After the particle counter is selected, the host computer 20 displays the information derived from the signals transmitted through the communication channel so that the operator can monitor the operating state of the selected particle counter in step S6. Thereby, the normal operational state of the selected particle counter can be determined. Once monitoring of the selected particle counter is completed, the operator may choose to select another particle counter in step S8. If chosen, another particle counter is selected by repeating step S4, and the newly selected particle counter is monitored by repeating step S6.

Figure 3:
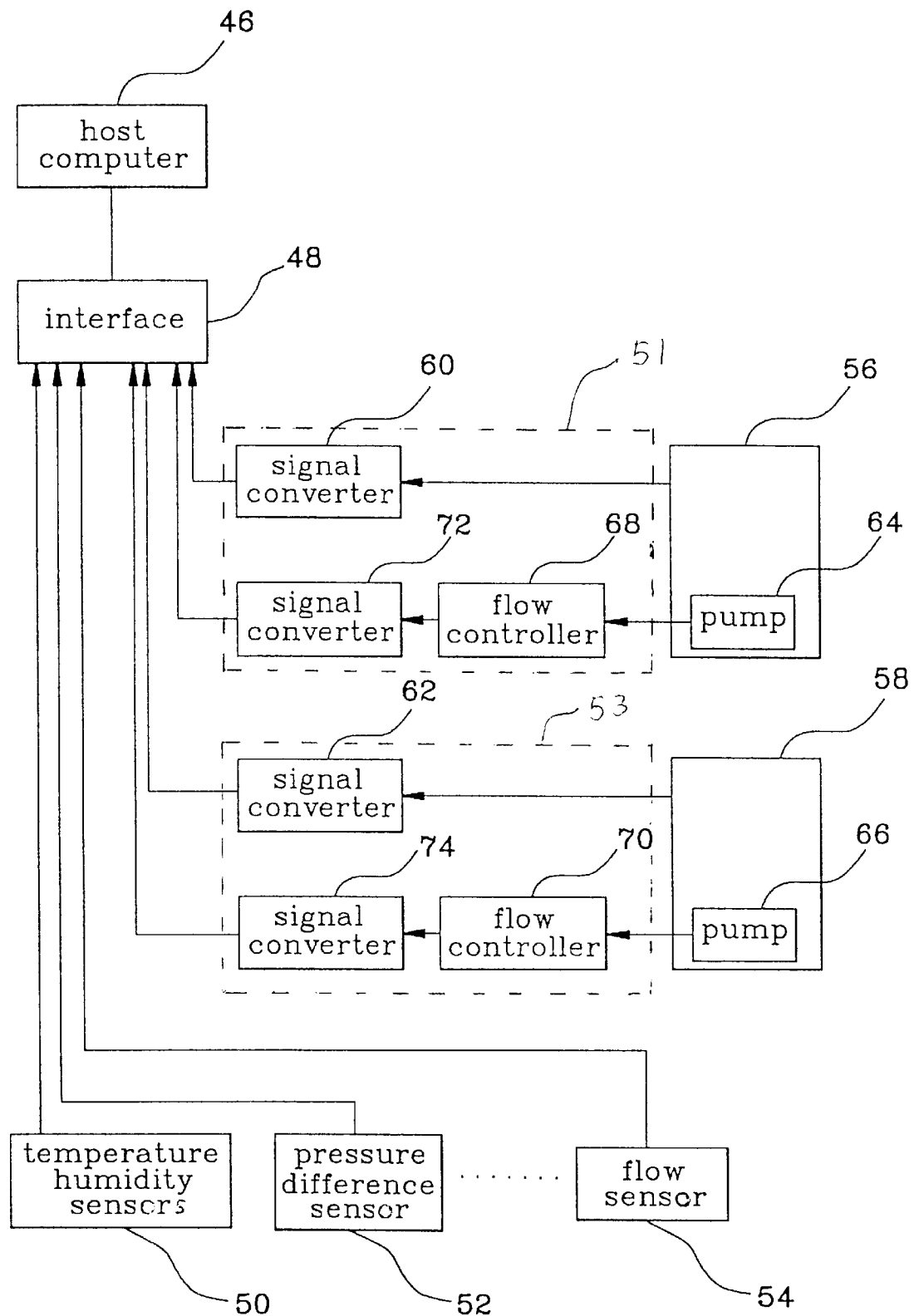
FIG. 3 is a block diagram of another embodiment of the monitoring system according to the present invention for monitoring a clean room regulating system using a direct interface.

Referring now to FIG. 3, portions of the direct interface embodiments are described in more detail. Here temperature and humidity sensors 50, a pressure difference sensor 52, and a flow rate sensor 54 are connected directly to an interface 48 which serves as the communication channel into the host computer 46. The particle counters 56 and 58 also communicate via the signal processors 51 and 53 to the same interface 48 which serves as the communication channel.

In the preferred embodiments, the signal processors 51 and 53 include first signal converters 60 and 62 and second signal converters 72 and 74. In the preferred embodiment of the direct interface embodiments, the connection of each signal converter 60, 62, 72, 74 into the interface 48 is done using the RS-232-C protocol. Alternatively, the interface 48 can be formed such that the connecting method is done using an X-series interface protocol.

The first signal converters 60, 62 convert the analog particle signals from the particle counters 56, 58 into digital signals using the RS-232-C protocol. The digital signals are input into the communication channel which includes the interface 48.

The particle counters 56 and 58 include respective pumps 64 and 66. Preferably, the signal processors 51 and 53 include flow controllers 68 and 70 for converting the pumping states of the pumps 64 and 66 into pumping signals. The second signal converters 72 and 74 convert the analog pumping signals to second digital signals using the RS-232-C protocol, and transfer the digital signals to the communication channel which includes the interface 48.

In the direct interface embodiments, the counted results and the pumping state of the particle counters 56 and 58 are derived from the digital signals directly input into the host computer 46 through the interface 48. The host computer 46 carries out the self-examination function, as previously described in reference to the host computer 20 in the LAN embodiments, in order to monitor the state of each particle counter 56, 58.

In order to conduct the self-examination functions on the host computer as illustrated in the LAN and direct interface embodiments of the present invention, software for monitoring the state of the regulating system including the particle counters, should be installed in the host computer. The host computer conducts the self examination function using the installed software. The state of the regulating system may be displayed graphically by date and time, and the data reflecting the monitoring state may be output through an output device.

The present invention monitors the condition of the clean room and the operational state of the regulating system components such as the particle counters. Therefore, appropriate air quality parameters can be easily and reliably regulated, monitored and maintained by clean room personnel. According to the present invention, monitoring various regulating systems installed inside a clean room is carried out centrally, on-line rather than on site, thereby providing more efficient and more reliable clean room management.

While certain embodiments of the present invention have been described in detail, it should be understood that various changes, substitutions and alterations can be made hereto by persons of ordinary skill in the art without departing from the spirit and scope of the invention as defined by the appended claims and their equivalents.

What is claimed is:

1. A monitoring system for monitoring a clean room regulating system, comprising:
    a particle counter comprising a pump having a pumping state for pumping a fluid containing particles, the particle counter producing an analog particle signal corresponding to an amount of particles detected, and producing a pump-state signal corresponding to the pumping state;
    a signal processor, coupled to the particle counter, that converts the analog particle signal into a first digital signal, converts the pump-state signal into an analog pumping signal, and converts the analog pumping signal into a second digital signal;
    a host computer that receives the first digital signal and derives the amount of particles detected, receives the second digital signal and derives the pumping state, and monitors the pumping state and the amount of particles detected; and
    a communication channel that transfers the first digital signal and the second digital signal from the signal processor to the host computer.

2. The monitoring system of claim 1, wherein the particle counter comprises an optical detector that produces the analog particle signal and produces a light-source signal indicative of an intensity of a light source used in the optical detector.

3. The monitoring system of claim 2, wherein the signal processor converts the light-source signal into a third digital signal, the communication channel transfers the third digital signal from the signal processor to the host computer, and the host computer receives the third digital signal and derives the intensity of the light source and monitors the intensity of the light source.

4. The monitoring system of claim 1, wherein the signal processor comprises:
    a first signal converter that converts the analog particle signal into the first digital signal;
    a flow controller that converts the pump-state signal into the analog pumping signal; and
    a second signal converter, coupled to the flow controller, that converts the analog pumping signal into the second digital signal.

5. The monitoring system of claim 4, wherein the first signal converter and the second signal converter use an X-series interface protocol for a network to produce the first digital signal and the second digital signal.

6. The monitoring system of claim 4, wherein the first signal converter and the second signal converter use a V-series interface protocol for a network to produce the first digital signal and the second digital signal.

7. The monitoring system of claim 6, wherein the V series interface protocol is a RS-232-C protocol.

8. The monitoring system of claim 1, wherein the communication channel comprises a local area network (LAN) node processor.

9. The monitoring system of claim 1, wherein the communication channel comprises a direct interface.

10. The monitoring system of claim 1, wherein the pump-state signal is indicative of an amount of fluid pumped.

11. A method of monitoring a clean room regulating system, comprising:
    choosing a self-examination function for checking a particle counter of a clean room regulating system;

selecting a particle counter to be monitored;

monitoring a first digital signal corresponding to an amount of particles detected by the selected particle counter, and a second digital signal corresponding to a pumping state of the selected particle counter;

executing the self-examination function using the amount of particles detected derived from the first digital signal and using the pumping state derived from the second digital signal; and displaying results of the executed self-examination function.

12. The method of claim 11, wherein the pumping state is related to an amount of fluid pumped.

13. A clean room regulating system comprising:

a pump that pumps a fluid containing particles in a clean room;

a particle converter, coupled to said pump, that produces a pump-state signal and a particle signal corresponding to an amount of particles detected in the fluid, the particle signal being analog;

a host computer that self-monitors and determines a condition of the clean room based on the pump-state signal and the particle signal and provides indication of the condition of the clean room; and a signal processor that digitally converts the particle signal and provides the digitally converted particle signal to said host computer as the particle signal, and that converts the pump-state signal into an analog pumping signal, digitally converts the analog pumping signal and Provides the, digitally converted pumping signal to said host computer as the pump-state signal.

14. The clean room regulating system of claim 13, further comprising a communication channel that transfers the digitally converted particle signal and the digitally converted pumping signal to said host computer.

15. The clean room regulating system of claim 14, wherein said communication channel comprises a local area network (LAN) node processor.

16. The clean room regulating system of claim 14, wherein said communication channel comprises a direct interface.

17. The clean room regulating system of claim 13, wherein said particle counter comprises an optical detector that produces the analog particle signal and a light source signal indicative of an intensity of a light source used in the optical detector.

18. The clean room regulating system of claim 17, wherein the light source signal produced by the optical detector is analog, the signal processor digitally converts the light source signal and provides the converted light source signal to said host computer, and said host computer monitors and determines the intensity of the light source.

19. The clean room regulating system of claim 13, wherein said host computer generates an alarm when the condition of the clean room is determined as outside a specified criteria.

20. The clean room regulating system of claim 13, wherein the pump-state signal is indicative of an amount of fluid pumped.

* * * * *